United States Patent [19]
Wood et al.

[11] 4,137,200
[45] Jan. 30, 1979

[54] CROSSLINKED HYDROPHILIC FOAMS AND METHOD

[75] Inventors: Louis L. Wood, Rockville, Md.; Kurt C. Frisch, Grosse Ile, Mich.

[73] Assignee: W. R. Grace & Co., New York, N.Y.

[21] Appl. No.: 805,458

[22] Filed: Jun. 10, 1977

Related U.S. Application Data

[63] Continuation-in-part of Ser. No. 404,823, Oct. 9, 1973, abandoned, which is a continuation-in-part of Ser. No. 250,012, May 3, 1972, abandoned.

[51] Int. Cl.$^2$ ................................................ C08J 9/02
[52] U.S. Cl. ...................................... 521/159; 521/176; 521/160; 521/905
[58] Field of Search ............... 260/2.5 AD, 2.5 AM, 260/2.5 A, 2.5 AP, 2.5 BD, 29.27 N

[56] References Cited

U.S. PATENT DOCUMENTS

| | | | |
|---|---|---|---|
| 2,726,219 | 12/1955 | Hill | 260/2.5 AP |
| 3,694,301 | 9/1972 | Gruenewald | 260/2.5 AD |
| 3,781,231 | 12/1973 | Janssen | 260/2.5 BE |
| 3,793,241 | 2/1974 | Kyle | 260/2.5 AM |

FOREIGN PATENT DOCUMENTS 1429711  3/1976  United Kingdom ............. 260/2.5 AD

*Primary Examiner*—Lewis T. Jacobs
*Attorney, Agent, or Firm*—Richard P. Plunkett; Philip M. Pippenger

[57] ABSTRACT

The invention disclosed is for new improved hydrophilic crosslinked polyurethane foams prepared by reacting a blend of a monomeric polyol and polyoxyalkylene glycol (the —OH groups of said blend being capped with a polyisocyanate) with large amounts of an aqueous reactant. The resultant foams may be characterized with a broad spectrum of improved properties including hydrolytic stability and tensile strength.

10 Claims, No Drawings

CROSSLINKED HYDROPHILIC FOAMS AND METHOD

This application for United States Letters Patent is a continuation-in-part of application Ser. No. 404,823 filed Oct. 9, 1973 which was in turn a continuation-in-part of application Ser. No. 250,012 filed May 3, 1972, both of which are now abandoned.

BACKGROUND OF THE INVENTION

This invention relates to new improved hydrophilic crosslinked polyurethane foams and to a method for their preparation. More particularly, the present invention relates to hydrophilic foams prepared from a capped polyoxyethylene polyol reactant having a defined average reaction functionality greater than two which is then admixed with large amounts of an aqueous reactant.

Numerous attempts have been made in the prior art to produce hydrophilic polyurethane foams. Typically, these attempts have been based on (1) inclusion of a separate hydrophilic additive into a hydrophobic polyisocyanate either during or after foaming; or (2) use of reactants such as polyoxyethylene polyol and a polyisocyanate with low, i.e. near stoichiometric amounts of water, and a catalyst; and (3) foams based on non-catalytic reactions using linear polyoxyethylene diols, diisocyanate and varying amounts of water.

DESCRIPTION OF THE INVENTION

It has now been surprisingly found, however, that improved new hydrophilic crosslinked polyurethane foams may be prepared simply by reacting a particular isocyanate-capped polyoxyethylene polyol with large amounts of an aqueous reactant. The thus generated foams are typically characterized by having a crosslinked, i.e. non-linear, molecular network which provides the product foams with a broad spectrum of improved properties.

Generally stated, the present crosslinked hydrophilic foam may be prepared by capping polyoxyethylene polyol with a polyisocyanate such that the capped product has a reaction functionality greater than two. The capped product is foamed simply by combining with an aqueous reactant. Optionally, the capped product and/or aqueous reactant may contain a suitable crosslinking agent if desired, in which case the capped polyoxyethylene polyol product may have a functionality approximating 2.

During capping, it is desirable that polyisocyanate be reacted with the polyol such that the reaction product, i.e. the capped product, is substantially void of reactive hydroxy groups while containing more than two reactive isocyanate sites per average molecule.

Polyoxyethylene polyol used as a reactant in preparing the capped product to be foamed may have a weight average molecular weight of about 200 to about 20,000, and preferably between about 600 to about 6,000, with a hydroxyl functionality of about 2 or greater, preferably from about 2 to about 8.

Polyoxyethylene polyol is terminated or capped by reaction with a polyisocyanate. The reaction may be carried out in an inert moisture-free atmosphere such as under a nitrogen blanket, at atmospheric pressure at a temperature in the range of from about 0° C. to about 120° C. for a period of time of up to about 20 hours depending upon the temperature and degree of agitation. This reaction may be effected also under atmospheric conditions provided the product is not exposed to excess moisture. The polyisocyanates used for capping the polyoxyethylene polyol include PAPI (a polyaryl polymethylenepolyisocyanate as defined in U.S. Pat. No. 2,683,730), tolyene diisocyanate, triphenylmethane-4,4',4" -triisocyanate, benzene-1,3,5-triisocyanate, toluene-2,4,6-triisocyanate, diphenyl-2,4,4'- triisocyanate, hexamethylene diisocyanate, xylene diisocyanate, chlorophenylene diisocyanate, diphenylmethane-4,4'-diisocyanate, naphthalene-1,5-diisocyanate, xylene-alpha, 3,3'-dimethyl-4,4'-biphenylene diisocyanate, 3,3'-dimethoxy-4,4'-biphenylene diisocyanate, 2,2',5,5'-tetramethyl-4,4'-biphenylene diisocyanate, 4,4'-methylenebis(phenylisocyanate), 4,4'-sulfonylbis (phenylisocyanate), 4,4'-methylene di-orthotolylisocyanate, ethylene diisocyanate, trimethylenediisocyanate, diicyclohexyl methane-4,4'-diisocyanate, isophorone diisocyanate, 1,6-hexamethylene diisocyanate, 2,2,4-trimethyl-1,6-hexane diisocyanate, and the like. Mixtures of any one or more of the above-mentioned organic isocyanates may be used as desired. The aromatic diisocyanates, aliphatic and cycloaliphatic diisocyanates and polyisocyanates or mixtures thereof which are especially suitable are those which are readily commercially available, have a high degree of reactivity and a relatively low cost.

Capping of the polyoxyethylene polyol may be effected using stoichiometric amounts of reactants. Desirably, however, an excess of polyisocyanate is used to insure complete capping of the polyol. Thus, the ratio of isocyanate groups to the hydroxyl groups used for capping is between about 1 to about 4 isocyanate to hydroxyl.

Isocyanate-capped polyoxyethylene polyol reaction products (prepolymers) employed in the present invention may be exemplified as follows. First, when water is the sole reactant with the isocyanate groups leading to chain growth during the foaming process, the isocyanate-capped polyoxyethylene polyol reaction product must have an average isocyanate functionality greater than 2 and up to about 8 or more depending upon the composition of the polyol and capping agent components. Secondly, when the isocyanate-capped polyoxyethylene polyol has an isocyanate functionality of only about two, then the water or aqueous reactant used may contain a dissolved or dispersed isocyanate-reactive crosslinking agent having an effective functionality greater than two. In this latter case, the reactive crosslinking agent is reacted with the capped polyoxyethylene polyol when admixed during and after the foaming process has been initiated. Thirdly, when the isocyanate-capped polyoxyethylene polyol has an isocyanate functionality of only about two, then a polyisocyanate crosslinking agent having an isocyanate functionality greater than two may be incorporated therein, either preformed or formed in situ, and the resultant mixture may then be reacted with water or aqueous reactant, optionally containing a dissolved or dispersed reactive isocyanatereactive crosslinking agent, leading to a crosslinked, infinite network hydrophilic polyurethane foam.

Several different modes may be used to prepare the prepolymer, i.e. the hydrophilic capped polyoxyethylene polyol reaction product having an average isocyanate functionality greater than two. In forming the prepolymer, blends or mixtures of the various polyols and/or polyisocyanates may be used as desired so long as the total average isocyanate functionality of the final urethane containing reaction product is greater than two.

One possible method for preparing the prepolymer is by reacting polyoxyethylene glycol having a reactive functionality equal to 2 with a molar excess of a diisocyanate which leads to an isocyanate-capped polyurethane product (A) having an isocyanate functionality of two. A polyol such as pentaerythritol having a reactive functionality equal to 4 is reacted with a large molar excess of a diisocyanate to form an isocyanate-capped polyurethane intermediate product (B) having an isocyanate functionality of four. By blending the two isocyanate-capped products thus prepared, i.e. products (A) and (B), in various molar proportions, the resulting product mixture has an average isocyanate functionality greater than two and on treatment with aqueous reactants will lead to new improved hydrophilic crosslinked polyurethane foams of the present invention. In addition, other monomeric or polymeric polyisocyanate crosslinking agents may be substituted for the tetraisocyanate product (B). Tolylene-2,4,6-triisocyanate having a reactive functionality of 3 is an example of a simple monomeric triisocyanate which may be usefully employed to achieve the same objective of imparting to the system an average isocyanate functionality greater than two.

A second method for preparing the prepolymer is to blend a generally linear polyol with a polyol having at least 3, and preferably from 3 to 8 hydroxyl groups (e.g. trimethylolpropane, trimethylolethane, glycerol, pentaerythritol or sucrose). Generally monomeric polyols having 3 to 4 hydroxyl groups per mole are employed. The blend is reacted with a sufficient amount of a polyisocyanate so that the resulting prepolymer is substantially void of unreacted hydroxyl groups, i.e. an excess of the polyisocyanate is preferably employed. The excess of polyisocyanate can range up to the point where about 4 isocyanate groups are employed for each hydroxyl group. It is also preferable to carry out the capping reaction incrementally, i.e. the initial amount of polyisocyanate added to the blend is less than what is theoretically necessary to react with all the hydroxyl groups of the polyol blend. For example, about 95% of theory can be employed initially. After allowing the initial polyisocyanate to react, a subsequent addition of polyisocyanate can be made to bring the total amount employed equal to theory (i.e. stoichiometric as described above) or preferably an excess (e.g. about 105–115% of theory) can be employed.

It has also been found that the capped polyoxyethylene polyol having an isocyanate functionality greater than two used to prepare a three-dimensional network polymer must be present in an amount sufficient to insure formation of the dimensional network. Thus, amounts of the capped polyoxyethylene polyol having an isocyanate functionality greater than two in the component to be foamed range from about 3% by weight of this component up to 100% by weight. Thus, it is possible to include a capped polyoxyethylene polyol having a terminal member with an isocyanate functionality of two, i.e. a diisocyanate in an amount from 0% by weight up to about 97% by weight of the component to be foamed. The maximum amounts of diisocyanate used are limited to that necessary to permit crosslinking to take place during foaming, as contrasted to formation of a linear polymeric structure, and the properties desired in the finally prepared foam.

The polyoxyethylene polyols used in this invention are water soluble reaction products derived from the polymerization of ethylene oxide in the presence of a polyfunctional starter compound such as water, ethylene glycol, glycerol, pentaerythritol, sucrose and the like. The molecular weights may be varied over a wide range by adjusting the relative ratios of ethylene oxide monomer to starter compound. The preferred molecular weight ranges have been described previously.

It is possible and sometimes desirable to incorporate various amounts of a relatively hydrophobic comonomer into the ethylene oxide based polymerization products. Thus, comonomers such as propylene oxide or butylene oxide may be copolymerized as a random copolymer, block-copolymer, or both, such that the copolymers remain hydrophilic while having other desirable features for certain applications, namely, improved low temperature flexibility, resistance to compression set, resiliency and the like. Up to about 40–60 mole percent but desirably about 25–45 mole percent of the relatively hydrophobic comonomer may be copolymerized with the ethylene oxide monomer and still yield hydrophilic crosslinked network foams when those products are used as polyol intermediates in practicing the present invention. Thus, throughout the text of this document, the term "polyoxyethylene polyol" is intended to include not only homopolymers of ethylene oxide but also hydrophilic copolymers of ethylene oxide such as those described above wherein all of these polyol derivatives have a hydroxyl functionality of about two or greater and an ethylene oxide content ranging from about 40 mole percent to about 100 mole percent, and preferably greater than about 55 mole percent.

To effect foaming and preparation of the crosslinked network polymer, the prepolymer or resin reactant is simply combined with a particular aqueous component. For simplicity, this isocyanate-capped reaction component will occasionally be referred to herein as "resin reactant".

The aqueous component may be water, a water slurry or suspension, a water emulsion, or a water solution having water soluble materials disposed therein. For convenience, the aqueous component is referred to herein as an aqueous reactant.

In contrast to typical polyurethane reactions such as those using catalyst or like promoters where one mole of —NCO is reacted with one half mole water, the present reaction proceeds simply with a large but controlled excess of water.

In typical polyurethane reactions known to the art, it is known to employ an excess of water to obtain improved properties. This has been observed at page 43 in the publication by Saunders and Frisch entitled "Polyurethanes", published by Interscience Publishers, where it is further observed that if less than stoichiometric amounts of water are used, the foam is more crosslinked, firmer, has lower elongation and higher density. A large excess of water, they observe, will use up the free isocyanate groups, leaving insufficient isocyanate available for effective crosslinking and resulting in the formation of many free amino end groups. As water content increases the foam density decreases, and above 30–50% excess water results in a marked decrease in physical properties.

The dramatic way in which the addition of water influences practice of the present invention is seen by consideration of the Water Index:

$$\frac{\text{equivalents of H}_2\text{O} \times 100}{\text{equivalents of NCO}} = \text{Water Index Value}$$

Here one must keep in mind that in polyurethane foaming reactions one mole of water ultimately consumes two NCO groups, i.e. 1.0 mole $H_2O$ = 2 equivalents —OH which react with 2 equivalents of NCO. A Water Index Value of 100 indicates the equivalents of water and equivalents of isocyanate are balanced. An Index of 95 indicates that there is a 5% shortage of water equivalents while an Index of 105 indicates a 5% surplus of water equivalents. A slight shortage of water equivalents (i.e. a slight excess of isocyanate), usually 3–5%, is common practice in the prior art, particularly with flexible foams.

In the present invention the amount of water employed should exceed 6.5 moles $H_2O$ per mole of NCO groups ($H_2O$ Index Value of 1300). The water employed can range up to about 390 moles $H_2O$/mole NCO groups ($H_2O$ Index Value 78,000). Thus, the available water content in the aqueous reactant is at least 6.5 and can fall within a range from about 6.5 to about 390 moles $H_2O$ per mole of NCO groups, i.e. an $H_2O$ Index Value of about 1300 to about 78,000 and desirably from about 4,000 to about 40,000, i.e. from about 20 to about 200 moles $H_2O$ per mole of NCO groups.

"Available water" in the aqueous reactant is that water accessible for reaction with the resin reactant, and which is exclusive of water which may layer during reaction, or supplemental water which may be necessary because of further water-absorptive or water-binding components or additives present in and forming the aqueous reactant.

The reaction temperature to effect foaming obviously is regulated by the viscosity of the resin reactant. The reaction may proceed either as a batch reaction or as a continuous reaction. Either the resin reactant may be poured into the aqueous reactant, or both may be combined simultaneously such as when using spray or froth application techniques. Both internal metering/mixing spray equipment and external mixing spray equipment can be used as desired. Excessive agitation of the aqueous phase may tear the foam structure and should be avoided if an integral structure is desired.

The use of large molar excesses of water in the aqueous reactant leads to several important advantages and improvements over the conventional polyurethane foam compositions of the prior art. For example, in conventional polyurethane foam compositions the water concentration must be carefully controlled to near the theoretical amount usually an amount much less than about an $H_2O$ Index Value of 400 (2.0 moles $H_2O$/NCO groups in the polyurethane reaction components). This low concentration dictates the use of a catalyst to promote the rate of the polymerization foaming reaction, and requires an intensive mixing step to achieve good mixing of reactants and catalyst so as to insure a controllable and uniform cellular product. In contrast, the present invention requires a very large excess of water, e.g. typically an $H_2O$ Index Value in excess of about 1300. Using this technique, the product quality and uniformity is not highly sensitive to accuracy of metering or mixing of the aqueous reactant, and the use of a polymerization catalyst or promoter is optional. Further, conventional polyurethane foam systems have limitations in spray-up thicknesses due to the fact that the high exotherm liberated during the foaming reaction tends to discolor the foams obtained, and foam thickness per single pass of the spray gun is limited to about 1 inch or less. In contrast, the compositions of the present invention have excess amounts of water present as a diluent which moderates the polymerization exotherm, permits the spray-up of foam thicknesses per single pass of substantially greater than one inch, without discoloration or overheating of the foam product. Further, conventional foam production, processing and spraying equipment requires the frequent and extensive use of toxic or flammable organic solvents such as acetone, tricresyl phosphate, methylene chloride and the like for cleaning and purging purposes. With the hydrophilic polyurethane components of the present invention, cleaning may be carried out conveniently with simple, non-toxic and non-flammable aqueous solutions. Moreover, in conventional polyurethane foam systems, both parts of the two-part formulation are comprised primarily or organic compounds. In the present invention, however, one of the two parts of the two-part formulations is primarily aqueous in nature, thereby facilitating metering and mixing, facilitating equipment clean-up, moderating reaction exotherm, reducing the fire hazard of the system during the spraying and other processing operations, and permitting the use of very simple and low cost foam fabrication equipment.

Because large amounts of water may be in the aqueous reactant during reaction, i.e. the present invention is not dependent upon a stoichiometric molar NCO-water type reaction, it is possible to combine a great variety of materials in the aqueous reactant which are otherwise not possible with limited water reacting systems.

The aqueous reactant may be used at temperatures from slightly above 0° C. to about 100° C. as desired. It is possible also to effect reaction of the resin reactant using water vapor or steam as the aqueous component.

Large amounts of many water soluble or water dispersible materials may be added to the aqueous reactant. These materials may be added to the aqueous reactant up to about 800% by weight of the amount of water in the aqueous reactant, depending of course on the particular material and its weight. Useful additives to the aqueous reactant include organic and inorganic salts, alcohols, amines, acids, polymer latices, resin or wax dispersions, flame retardants, fungicides, fillers, blowing agents, fibers, cellulosics, surfactants, biostats, pigments, dyes, zeolites, enzymes, proteins, chelates, hydrogenation or cracking catalysts, thickeners, stabilizers, promoters or the like. By homogeneously distributing these materials in the aqueous reactant, it is possible to effect wide distribution of these materials throughout the finally prepared foam. Some or all of the above additives may also be combined into the resin reactant if desired.

It is possible to dispose the resin reactant onto fabrics, either woven or non-woven, paper, or the like with the resin reactant appearing either on the surface or imbibed as described. Thus, upon contact of such material with water, water spray, steam or moist air, it is possible to prepare tough, flexible to rigid, soft to coarse products. Such products using the present hydrophilic foams may be rendered somewhat repellent of liquid water yet breathable and thus permeable to water vapor.

The present foams have great utility for decorative, cushioning, insulative, sound deadening, protective and/or fire retardant surfaces. Accordingly, these foams may form strippable coatings for protecting articles during handling and shipment. Also, because the present crosslinked foams are easily sterilized, they find great utility as household, industrial and/or biomedical sponges. The feature of water vapor permeability of these sponges resulting from the hydrophilic nature of the polyoxyethylene polyol reactant, renders them attractive for apparel.

The present foams may be prepared by using aqueous slurries of fine vermiculite, ceramic or inorganic powders, silica, clays and the like, solutions of borates, phosphates and the like, and of oil-in-water emulsions.

These foams may contain soil, nutrients, and/or fillers for horticultural applications including use as a matrix for plant growth. For this purpose, the present foams are effective for supporting seedlings which may be simply transplanted without root damage.

Catalysts, antioxidants and other chemical reactants may be supported on the foams generated by practice of this invention. Such structures find effective application in a variety of chemical and biological arts including enzymatic reactions, fuel cells, filters, water or blood purification, extraction applications, in separation systems and the like.

A wide variety of solid materials may be added to the present foams to produce changes in properties, particularly to improve load-bearing characteristics. These solid materials which may be added include finely divided solid particles or powders, powdered metals, activated charcoal, carbon blacks, large granular or particulate solids and fibrous materials. Suitable fillers of this type include barium sulfate, alumina hydrate, zircon sand, calcium carbonate and the like and organic fillers such as shredded cornstalks, straw, hay and the like.

Various conventional radiation barrier materials such as lead, boron hydrides, hafnium titanate and the like may also be combined with the present foams by way of the aqueous reactant.

Although foaming of the present resin reactant is effected simply, it is also possible to add, although not necessary, supplemental foaming materials such as those well known to the artificial sponge foaming art.

The following examples will aid in explaining, but should not be deemed as limiting, practice of the present invention. In all cases, unless otherwise noted, all parts and precentages are by weight.

EXAMPLE 1

A prepolymer was prepared by admixing 2 molar equivalents of polyethylene glycol having an average molecular weight of 1,000 (PEG — 1,000) and one molar equivalent of trimethylolpropane (TMOP). The admixture was dried at 100°–110° C. under a pressure of 5–15 Torr to remove water. The resulting dried mixture was slowly added over a period of about one hour to a vessel containing 6.65 molar equivalents of toluene diisocyanate (TDI) while stirring the TDI and polyol mixture. The temperature was maintained at 60° C. The mixture was maintained at 60° C. with stirring for three additional hours. Then an additional 1.05 molar equivalent of TDI was added with stirring over a period of about one hour while maintaining the temperature at 60° C. The final reaction mixture contained a 10% molar excess of TDI. All hydroxyl groups were capped with isocyanate and some chain extension occurred because of crosslinking of the polyols with TDI.

Hydrophilic foams have been prepared from the above prepolymer using large amounts of water as described previously. These foams exhibit good physical properties, and various materials as described above can be incorporated into the aqueous phase when preparing the foams.

EXAMPLE 2

A prepolymer was prepared as in Example 1 with the exception that 0.66 molar equivalents of TMOP were employed for every 2 equivalents of PEG — 1,000. In the initial capping reaction with TDI, the amount of TDI employed was about 92% of that theoretically required to cap all hydroxyl groups in the polyol mixture. Subsequently, an additional 13% TDI was added to provide a theoretical molar excess of about 5%.

EXAMPLE 3

Comparison With Foams Adapted From U.S. Pat. No. 3,793,241

U.S. Pat. No. 3,793,241 in Example 2 describes preparation of foams from a mixture of polyethylene glycol (PEG — molecular weight 1000) end-capped with toluene diisocyanate. Mondur MRS brand of poly(methylenephenylene isocyanate) is admixed with a fluorochemical surfactant, as described in U.S. Pat. No. 3,378,399, and bentonite, t-butylphenyl calcium octoate and phenyl mercuric acetate. The resulting admixture is foamed using a mixture of ice and water.

To illustrate foams prepared as in Example 2 of U.S. Pat. No. 3,793,241 but using only a surfactant and the isocyanates, a PEG (molecular weight 1,000) was end-capped with 115% theory of TDI. 100 parts of the capped PEG were admixed with 5 parts of Mondur MRS having an isocyanate functionality of 2.8. The resulting prepolymer was foamed using a mixture of ice and water.

As a comparison, a second prepolymer was prepared using trimethylolpropane (TMOP) capped with TDI, in place of the Mondur MRS taught in U.S. Pat. No. 3,793,241. The method of preparation was as follows: a mixture of 666 parts of PEG — 1,000 and 13.9 parts of TMOP was dried at 105° C. for 7 hours at 1.5 Torr. The dried mixture was added to 320 parts of TDI (112% theory) at 60° C. over a period of 20 minutes, and the mixture was heated at 60° C. for 5.25 hours and then allowed to stand for 16 hours. The viscosity was 9,200 centipoises, and the NCO meq/g. was found to be 2.04 (theory 2.04). The theoretical cross-link density of both the prepolymers, i.e. the one containing capped TMOP, and the prepolymer using Mondur MRS was 0.10 cross-links per 1,000 molecular weight.

A number of foams were made from the above mixtures using various surfactants. In all cases the prepolymers were foamed by admixture with 100 parts of a mixture of 75 parts ice and 25 parts water.

Further descriptions of the runs and the physical properties of the resulting foams are set forth in Table 1 below. The amounts of reactants employed are based on parts by weight of the total reaction mixture.

TABLE 1

| | Description of Prepolymer and Foaming | Diameter Shrinkage[4],% | Density (lbs/ft.[3])[5] | Dry Tensile Properties[6] | | | Wet Tensile Properties[6] | | | LOI[7] |
|---|---|---|---|---|---|---|---|---|---|---|
| | | | | Modulus at 1% Elong. Psi | Tensile at Failure Psi | Elong. Fail % | Modulus at 1% Elong. Psi | Tensile at Failure Psi | Elong. Fail % | |
| 1) | 107.3 parts of capped PEG/TMOP prepolymer, 1 part heptafluorobutyramide[1], 75 parts ice, 25 parts H$_2$O | 16 | 9.17 | 63 ± 12 | 60 ± 3.1 | 315 ± 45 | 39 ± 10.8 | 25 ± 4.2 | 140 ± 18 | 0.239 |
| 2) | 100 parts of capped PEG, 5 parts Mondur MRS, 1 part heptafluorobutyramide[1], 75 parts ice, 25 parts H$_2$O | 13 | 9.67 | 29 ± 8 | 28 ± 7.2 | 250 ± 49 | 12 ± 2.8 | 10 ± 3.8 | 144 ± 28 | 0.291 |
| 3) | 107.3 parts of capped PEG/TMOP prepolymer; 1 part Pluronic L-62[2]; 75 parts ice, 25 parts H$_2$O | 15 | 9.42 | 35 ± 1.6 | 60 ± 6.0 | 614 ± 67 | 35 ± 7.0 | 37 ± 3.2 | 208 ± 65 | 0.251 |
| 4) | 100 parts of capped PEG; 5 parts Mondur MRS, 1 part Pluronic L-62[2]; 75 parts ice, 25 parts H$_2$O | 16 | 5.76 | 18 ± 1.6 | 24 ± 1.9 | 395 ± 49 | 10 ± 1.3 | 10 ± 1.1 | 139 ± 11 | 0.304 |
| 5) | 107.3 parts of capped PEG/TMOP prepolymer; 1 part L-520[3]; 75 parts ice, 25 parts H$_2$O | 15 | 8.89 | 59 ± 1.2 | 60 ± 6.7 | 508 ± 64 | 31 ± 3.0 | 34 ± 0.4 | 239 ± 28 | 0.267 |
| 6) | 100 parts capped PEG; 5 parts Mondur MRS, 1 part L-520[3]; 75 parts ice, 25 parts H$_2$O | 17 | 6.62 | 20 ± 3.6 | 32 ± 4.3 | 452 ± 171 | 13 ± 2.3 | 15 ± 0.9 | 183 ± 33 | 0.287 |
| 7) | 100 parts capped PEG; 8.9 parts of capped TMOP; 1 part heptafluorobutyramide[2]; 100 parts H$_2$O (25 parts water, 75 parts ice) | 11 | 12.6 | 65 ± 27 | 47 ± 13 | 304 ± 39 | 40 ± 3 | 41 ± 4.9 | 201 ± 55 | 0.285 |
| 8) | 100 parts capped PEG; 5 parts Mondur MRS; 1 part heptafluorobutyramide[1]; 100 parts H$_2$O (25 parts water, 75 parts ice) | 13 | 5.9 | 21 ± 2.4 | 27 ± 5.1 | 468 ± 17 | 12 ± 3.9 | 15 ± 4.2 | 334 ± 49 | 0.272 |

[1]Heptafluorobutyramide surfactant was prepared as described in U.S. Pat. No. 3,793,241.
[2]Surfactant L-62 is Pluronic L-62 (BASF Wyandotte) wherein polypropylene oxide is end-capped with ethylene oxide.
[3]L-520 is Union Carbide L-520 oxyalkylated silicone type surfactant.
[4]Shrinkage measurements were determined on samples foamed in either 12 or 32 ounce wax-coated cups having a base diameter of either 4.90 or 8.19 cm. respectively. The foam was removed intact and the base diameter recorded. Following drying in a vacuum oven for 16 hours at 60–70° C. at 150 Torr, the base diameter was again measured. Shrinkage was determined by the following formula % shrinkage = $\frac{\text{(original diameter)} - \text{(dried diameter)}}{\text{(original diameter)}} \times 100\%$

[5]Density measurements were carried out according to ASTM 1564-69 (Sections 75–80).
[6]The dry tensile properties were carried out according to ASTM 1564-69 (Sections 88–94). Wet tensile properties were determined by ASTM 1564-69 (Sections 88–94) except that the tensile species were sprayed with water (to saturation) prior to conducting the tests.
[7]The Limiting Oxygen Index (LOI) is determined by ASTM D 2963-74 modified as set forth in Batorewicz and Hughes, Journal of Fire and Flammability 2, 259 (1971).

In Table 1 the odd numbered runs are foams prepared according to the present invention while the even numbered foams were prepared using the process adapted from Example 2 of U.S. Pat. No. 3,793,241. Comparing Runs 1 and 2 in the above table, even though the density for the foam of Run 2 is slightly higher than Run 1, the tensile properties of the foam in Run 1 are significantly better. Comparing Runs 3 and 4, the tensile properties of the foam of Run 3 are significantly better than those of Run 4 even though allowance is made for the increased density of the foams of Run 3 as compared with Run 4 (9.42 vs. 5.76). Comparing Runs 5 and 6, again the tensile properties of the foams of Run 5 are significantly better than those of Run 6 even though allowance is made for the increased density of the foam of Run 5 over that of Run 6.

The data for Limiting Oxygen Index in the above table indicates that the even numbered foams were slightly superior to the odd numbered foams.

In another series of runs, TMOP was separately capped with TDI and subsequently combined with the capped PEG. Using the same crosslinking density as in Runs 1–6 above, a foam was prepared. For purposes of comparison a foam was also prepared as in Run 2 above. The results are set forth in Runs 7 and 8 in Table 1.

Comparison of the tensile properties in Runs 7 and 8 indicates that the foams are essentially equivalent when allowance is made for density differences. The tensile properties of Run 8 are superior to those of Run 2 although the foam of Run 1 is significantly better than either foams 2 or 8. The difference between the foams of Runs 1 and 7 is that in Run 1 the polyol (TMOP) and PEG were admixed prior to capping (i.e. the polyisocyanate crosslinking agent was formed in situ) whereas in Run 7 the TMOP crosslinker and the PEG were capped separately.

The foams prepared in Examples 1 and 2 above were tested by immersion of samples in boiling water. After 2 hours, the foam from Run 1 was left almost unchanged whereas the foam of Run 2 showed considerable shrinkage along with simultaneous thinning of cell walls and was at the point of disintegration. To complete the test the samples were maintained in boiling water until disintegration of one of the samples occurred. After 12 hours, the sample from Run 2 had disintegrated completely whereas the sample from Run 1 remained intact.

The foams from Runs 1 and 2 were also tested in an autoclave providing steam at 105° C. The foams were examined after 40 and after 80 minutes inside the autoclave. The foam from Run 1 remained intact even after 80 minutes. The foam of Run 2 became tacky after 40 minutes with the tack increasing noticeably after 80 minutes. The rebound or resilience of the foam from Run 2 was also reduced after 80 minutes indicating that hydrolysis was occurring both at the surface and at interior portions of the foam. The rebound characteristic of the foam of Run 1 remained essentially constant throughout the autoclave test.

EXAMPLE 4

Foams were prepared as in Runs 7 and 8 of Example 3 with the exception that a different fluorocarbon surfactant (Zonyl by E. I. DuPont Co.) was employed. This surfactant is not believed to be one of the types of fluorocarbon surfactants described in U.S. Pat. No. 3,793,241 although the composition of the surfactant was not actually ascertained. Preparation of the foams and physical properties thereof are set forth in the following table. From the following table it can be seen that foams prepared with Zonyl FSC were roughly comparable whether employing Mondur MRS or the polyisocyanate crosslinkers of the invention, i.e. TMOP capped with TDI and glycerine capped with TDI.

The foams of Run 7 of Example 3 and Runs 2 and 3 of Example 4 were prepared by capping the polyol (TMOP or glycerol) with TDI prior to admixture with the capped PEG. Foams produced by this technique are generally inferior to those where the polyol and polyoxyalkylene ether are blended prior to capping.

TABLE II

| Run | Composition of Foaming Mixture | Physical Properties of Foams | Tensile Properties (Dry) | | | Tensile Properties (Wet) | | |
|---|---|---|---|---|---|---|---|---|
| | | | Modulus at 1% Elong. Psi | Tensile at Failure Psi | Elong. to Fail, % | Modulus at 1% Elong. Psi | Tensile at Failure Psi | Elong. to Fail, % |
| 1 | 100 g. of PEG capped with TDI; 5 g. Mondur MRS; 1 g. of Zonyl FSC; 100 g. H₂O (75 g. ice and 25 g. water) | The cream time was 15 seconds, rise time 15 mins., diameter shrinkage 12%, density 7 lbs/ft³, LOI 0.315 ± 0.002. | 18 ± 1.4 | 26 ± 8 | 675 ± 15 | 8 ± 2.3 | 16 ± 4.5 | 676 ± 106 |
| 2 | 100 g. of PEG capped with TDI; 8.9 g. of TMOP capped with TDI; 1 g. of Zonyl FSC; 100 g. H₂O (75 g. ice and 25 g. water) | The cream time was 15-20 seconds, rise time 15 mins., diam. shrinkage 13%, density 10.6 lbs/ft³, LOI 0.238 ± 0.002. | 16 ± 4.5 | 20 ± 1.3 | 430 ± 81 | 10 ± 2.5 | 10 ± 0.7 | 217 ± 13 |
| 3 | 100 g. of PEG capped with TDI; 9.3 g. of glycerine capped with TDI; 1 g. of Zonyl FSC; 100 g. H₂O (75 g. ice and 25 g. water) | The cream time was about 5 seconds, rise time 15 mins., diam. shrinkage 12%, density 4.2 lbs/ft³, LOI 0.254 ± 0.002. | 15 ± 2.4 | 16 ± 2.1 | 360 ± 58 | 12 ± 2.0 | 9 ± 1.2 | 16 ± 216 |

What is claimed is:

1. A crosslinked hydrophilic foam having a three-dimensional network comprising the reaction product of
   A. isocyanate capped prepolymers consisting of a mixture of
      (1) an isocyanate capped hydrophilic polyoxyethylene diol, said diol having an ethylene oxide content of at least 40 mole percent; and
      (2) an isocyanate capped polyol having a hydroxyl functionality in the range 3 to 8 prior to capping; said isocyanate capped polyol being present in an amount in the range 2.9 to 50% by weight of (1) and (2);
   B. 3.2 to 7.9% by weight of A and B of a polyisocyanate having an isocyanate functionality in the range 2.0 to 2.8; and
   C. 6.5 to 390 moles of water for each mole of unreacted isocyanate.

2. A foam as in claim 1 wherein the polyol is trimethylolpropane.

3. A foam as in claim 1 wherein the polyol is glycerol.

4. A foam as in claim 1 wherein the polyol is pentaerythritol.

5. The process of forming a crosslinked hydrophilic urethane foam which comprises admixing a hydrophilic polyoxyethylene diol having an ethylene oxide content of at least 40 mole percent with a polyol having a hydroxyl functionality in the range 3 to 8, said polyol being present in the admixture in an amount in the range 1.0 to 20% by weight, reacting with the admixture at a temperature in the range 0 to 120° C. an amount of a polyisocyanate having an isocyanate functionality in the range 2.0 to 2.8 equal to 1.8–1.9 NCO to OH equivalents for a time sufficient to cap substantially all the hydroxyl groups of the admixture, adding additional polyisocyanate having an isocyanate functionality in the range 2.0 to 2.8 to provide 0.1–0.3 equivalents of NCO per initial equivalent of OH in excess of the theoretical amount necessary to react with the hydroxyl groups and thereafter adding 6.9 to 390 moles of water for each mole of unreacted isocyanate in the admixture.

6. A method as in claim 5 wherein the polyol is trimethylolpropane.

7. A method as in claim 5 wherein the polyol is glycerol.

8. A method as in claim 5 wherein the polyol is pentaerythritol.

9. A crosslinkable hydrophilic urethane foam forming composition upon the addition of an aqueous reactant comprising
   (1) a isocyanate capped hydrophilic polyoxyethylene diol, said diol having an ethylene oxide content of at least 40 mole percent;
   (2) an isocyanate capped polyol having a hydroxyl functionality in the range 3 to 8 prior to capping; said isocyanate capped polyol being present in an amount in the range 2.9 to 50% by weight of (1) and (2); and
   (3) 3.2 to 7.9% by weight of the composition of a polyisocyanate having an isocyanate functionality in the range 2.0 to 2.8.

10. The process of forming a crosslinkable hydrophilic urethane foam forming composition which comprises admixing a hydrophilic polyoxyethylene diol having an ethylene oxide content of at least 40 mole percent with a polyol having a hydroxyl functionality in the range 3 to 8, said polyol being present in the admixture in an amount in the range 1.0 to 20% by weight, reacting with the admixture at a temperature in the range 0 to 120° C. an amount of a polyisocyanate having an isocyanate functionality in the range 2.0 to 2.8 equal to 1.8–1.9 NCO to OH equivalents for a time sufficient to cap substantially all the hydroxyl groups of the admixture and thereafter adding additional polyisocyanate having an isocyanate functionality in the range 2.0 to 2.8 to provide 0.1–0.3 equivalents of NCO per initial equivalent of OH in excess of the theoretical amount necessary to react with the hydroxyl groups.

* * * * *